United States Patent
Ghalili et al.

(10) Patent No.: US 11,931,458 B2
(45) Date of Patent: *Mar. 19, 2024

(54) EXOSOME SYSTEMS, PRODUCTS AND METHODS

(71) Applicants: Babak Ghalili, New York, NY (US); Keyon Janani, Baton Rouge, LA (US); Peter Scherp, Denham Springs, LA (US); John Borja, Keyport, NJ (US)

(72) Inventors: Babak Ghalili, New York, NY (US); Keyon Janani, Baton Rouge, LA (US); Peter Scherp, Denham Springs, LA (US); John Borja, Keyport, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/571,658

(22) Filed: Jan. 10, 2022

(65) Prior Publication Data

US 2022/0218609 A1     Jul. 14, 2022

Related U.S. Application Data

(60) Provisional application No. 63/135,817, filed on Jan. 11, 2021.

(51) Int. Cl.
| | |
|---|---|
| *A61K 9/127* | (2006.01) |
| *A61K 31/685* | (2006.01) |
| *A61K 35/28* | (2015.01) |
| *A61K 35/50* | (2015.01) |
| *A61K 47/20* | (2006.01) |
| *A61K 47/64* | (2017.01) |
| *C12N 5/073* | (2010.01) |
| *C12N 5/0775* | (2010.01) |

(52) U.S. Cl.
CPC ............ *A61K 9/127* (2013.01); *A61K 31/685* (2013.01); *A61K 35/28* (2013.01); *A61K 35/50* (2013.01); *C12N 5/0605* (2013.01); *C12N 5/0662* (2013.01); *A61K 47/20* (2013.01); *A61K 47/645* (2017.08); *C12N 2500/62* (2013.01)

(58) Field of Classification Search
None
See application file for complete search history.

(56) References Cited

U.S. PATENT DOCUMENTS

| | | | |
|---|---|---|---|
| 2012/0269899 A1 | 10/2012 | Ladizinsky | |
| 2014/0308217 A1* | 10/2014 | Schaeffer-Korbylo | ............ A61Q 11/00 424/50 |
| 2015/0023908 A1* | 1/2015 | Al-Qahtani | ......... A61K 8/0254 424/85.2 |
| 2017/0128355 A1 | 5/2017 | Giampapa et al. | |
| 2017/0209365 A1 | 7/2017 | Cho et al. | |
| 2021/0177757 A1 | 6/2021 | Bolen et al. | |
| 2021/0338584 A1 | 11/2021 | Richardson et al. | |

FOREIGN PATENT DOCUMENTS

| | | |
|---|---|---|
| WO | 2012168050 A1 | 12/2012 |
| WO | 2019199803 A1 | 10/2019 |
| WO | 2020223349 A1 | 11/2020 |
| WO | 2021026353 A3 | 3/2021 |
| WO | 2021062317 A1 | 4/2021 |

OTHER PUBLICATIONS

Translation of Lorenz et al., WO 2012/168050, retrieved from https://patentscope.wipo.int/search/en/detail.jsf?docid=WO2012168050&_cid=P10-LDNZZM-93449-1 on Feb. 2, 2023. (Year: 2012).*

Burke et al, "Stem Cell-Derived Exosomes: A Potential Alternative Therapeutic Agent in Orthopaedics", Stem Cells International, pp. 1-6, Article ID 5802529, http://dx.doi.org/10.1155/2016/5802526, 2016, 6 pages.

Keshtkar et al, "Mesenchymal stem cell-derived extracellular vesicles: novel frontiers in regenerative medicine", Stem Cell Research & Therapy, pp. 1-9, https://doi.org/10.1186/s13287-018-0791-7, 2018, 9 pages.

Phinney et al, "Concise Review: MSC-Derived Exosomes for Cell-Free Therapy", Tissue-Specific Stem Cells, pp. 851-858, Published Mar. 7, 2017, 8 pages.

Taghizadeh et al, "Towards Clinical Applications of Umbilical Cord Derived Mesenchymal Stem Cells", Perinatal Stem Cells, pp. 347-359 , DOI: 10.1007/978-1-4939-1118-9_31 , 2014, 13 pages.

Zhang et al, "Exosomes: biogenesis, biologic function and clinical potential", Cell & Bioscience, pp. 1-18, https://doi.org/10.1186/s13578-019-0282-2, 2019, 18 pages.

Antimisiaris et al, "Exosomes and Exosome-Inspired Vesicles for Targeted Drug Delivery", Pharmaceutics, Nov. 6, 2018, vol. 10, doi: 10.3390/pharmaceutics10040218, 40 pages.

Hyldgaard et al., "The Antimicrobial Mechanism of Action of Epsilon-Poly-L-Lysine", Applied and Environmental Microbiology, Oct. 10, 2014, vol. 80, No. 24, doi: 10.1128/AEM.02204-14, 13 pages.

International Search Report and Written Opinion of the International Searching Authority, United States Patent and Trademark Office, Application No. PCT/US2022/011893, dated Apr. 27, 2022, 9 pages.

(Continued)

*Primary Examiner* — Allison M Fox

(74) *Attorney, Agent, or Firm* — Ziegler IP Law Group

(57) ABSTRACT

The present disclosure relates to exosome systems and compositions and preservative systems and compositions as well as methods of use and methods of manufacturing of them.

6 Claims, No Drawings

(56) References Cited

OTHER PUBLICATIONS

International Search Report and Written Opinion of the International Searching Authority, United States Patent and Trademark Office, Application No. PCT/US2022/023464, dated Jul. 14, 2022, 18 pages.
Lin et al, "Exosome-Liposome Hybrid Nanoparticles Deliver CRISPR/Cas9 System in MSCs", Advanced Science, Jan. 30, 2018, vol. 5, Issue 4, 1700611, DOI: 10.1002/advs.201700611, 9 pages.
United States Patent and Trademark Office, Non-Final Office Action, U.S. Appl. No. 17/713,679, dated Oct. 5, 2022, 22 pages.
Xing et al., "Oxygen Solubility Diffusion Coeffeicient and Solution Viscosity" Chapter 1, Rotating Electrode Methods and Oxygen Reduction Electrocatalysts, 2014, 31 pages.

\* cited by examiner

EXOSOME SYSTEMS, PRODUCTS AND METHODS

CROSS-REFERENCE TO RELATED APPLICATIONS

This application claims priority to and the benefit of U.S. Provisional Patent Application Ser. No. 63/135,817 filed Jan. 11, 2021, the disclosure of which is incorporated herein by reference in its entirety.

FIELD

The aspects of the present disclosure relate to exosome systems and products as well as methods of making and using same.

BACKGROUND

Exosomes are vesicles secreted by many cell types. They have a bi-lipid membrane and can be about 30 to about 100 nm in size. Exosomes are of endocytic origin and are normally released by the cells in which they are formed into the extracellular environment. They can contain various cellular products such as lipids, proteins and genetic materials that are being discarded by the cells in which they are created.

Exosomes are fragile vesicles and maintaining their integrity in a suitable environment is necessary so that they can be utilized in difficult therapeutic compositions.

SUMMARY

In one embodiment, a composition is provided. The composition includes a plurality of exosomes; dimethyl sulfoxide; and epsilon poly L-lysine.

In one embodiment, a composition is provided. The composition includes a plurality of exosomes; a plurality of liposomes dimethyl sulfoxide; and epsilon poly L-lysine.

In another embodiment, a method of making an exosome composition that maintains the structure and integrity of the exosomes is provided. The method includes mixing water; a plurality of exosomes; a lipid that forms liposomes without the use of alcohol; dimethyl sulfoxide; and epsilon poly L-lysine.

DETAILED DESCRIPTION

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by embodiments of the present disclosure. As used herein, "about" may be understood by persons of ordinary skill in the art and can vary to some extent depending upon the context in which it is used. If there are uses of the term which are not clear to persons of ordinary skill in the art, given the context in which it is used, "about" may mean up to plus or minus 10% of the particular term.

The terms "%", "% by weight", "weight %" and "wt %" are all intended to mean unless otherwise stated, percents by weight based upon a total weight of 100% end composition weight. Thus 10% by weight means that the component constitutes 10 wt. parts out of every 100 wt. parts of total composition.

The term "pharmaceutically acceptable" means that which is useful in preparing a pharmaceutical composition that is generally non-toxic and is not biologically undesirable and includes that which is acceptable for veterinary use and/or human pharmaceutical use.

The term "topically acceptable" means the compound, substance or device may be administered to or onto the surface of a patient, including the skin or other accessible tissues, without substantial harmful effects to the body part and/or its surfaces.

The terms "treating" and "effective amount", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above. The term "treating" also includes adjuvant and neo-adjuvant treatment of a subject.

All of the embodiments included here are with the proviso that the sum of ingredients in the exemplary compositions does not exceed 100%.

The aspects of the present disclosure relate to exosome systems and compositions and preservative systems and compositions and methods of forming them in which the viable (i.e., active) structure and integrity of the exosomes and its contents can be maintained using additional components to preservative the exosomes to deter disadvantageous occurrences such as, for example, clumping. Aspects of the present disclosure also include fluid mixtures and compositions of exosomes and exosomes including liposomes and both also include additional components to preservative and maintain the structure and integrity of the exosomes and its contents and the liposomes as well as prevent deleterious conditions such as, for example, clumping of the exosomes.

A "liposome" is a generic term encompassing a variety of single and multilamellar lipid vehicles formed by generating enclosed lipid bilayers or aggregates. Liposomes may have vesicular structures with a bilayer membrane, generally comprising a phospholipid, and an inner medium that generally comprises an aqueous composition. Liposomes for the present disclosure may include unilamellar liposomes, multilamellar liposomes, and multivesicular liposomes and may be positively charged, negatively charged, or neutrally charged.

The exosomes included in embodiments of the present disclosure preferably are obtained or extracted from different sources including various cell types, for example, placental cells and stem cells. The exosomes from stem cells contain biomolecules that are different from the exosomes of other cells. Exosomes from urine, blood or plasma serum, or epithelial cells or differentiated cells, will not have the same regenerative effect as compared to stem cell exosomes (e.g., mesenchymal stem cells (MSCs) exosomes). Exosomes are generated by all living cells. The contents of stem cell exosomes (e.g., MSC exosomes) is dependent on where they are coming from. Stem cells have a certain regenerative effect when injected. These effects can be replicated by using exosomes from stem cells. The regenerative effect of stem cells likely comes from the exosome itself and its contents. Mesenchymal stem cell exosomes transfer functional cargos like miRNA and mRNA molecules, peptides, proteins, cytokines and lipids from MSCs to the recipient cells. These exosomes participate in intercellular communication events and contribute to the healing of injured or diseased tissues and organs. and, as a result, can be more beneficial. Exosome extraction can be performed using different known types of centrifugation and ultracentrifugation. After the centrifugation and ultracentrifugation steps, they can be further purified using additional known procedures including, for example, gel filtration. Exosomes can be present in embodiments of the present disclosure in an amount of about 0.25 wt % to about 1.00 wt %, about 0.50 wt %; or about 10 million to about 20 trillion exosomes, or about 1 billion exosomes per 1 ml volume.

While all mammalian cells secrete exosomes, only exosomes derived from stem cells are currently considered therapeutic. Stem cells can be cultured in many different ways. This includes 2D culturing, which typically occurs in flasks or cylinders. Three dimensional culturing is facilitated in bioreactors, which can include stirred tank and hollow fiber setups. Independent of the culturing method of the stem cell culture, the exosomes are secreted into the culture medium in which they are propagated by the stem cells. The culturing method can determine the concentration of exosomes per volume culture medium.

In order to isolate stem cell derived exosomes, the conditioned culture medium undergoes a procedure that concentrates the exosomes and ultimately removes the culture medium which then can be replaced with the desired medium for various pharmaceutical and/or cosmetic compositions and uses, e.g. about 0.9 wt % sodium chloride for injection (either exosomes by themselves in saline or with other therapeutic compounds (in surrounding medium or incorporated into the exosome itself) that can, for example, enhance penetration, i.e. liposomes, vitamins, minerals, other therapeutic compounds) or phosphate buffered saline for other applications such as cosmetics (e.g., an exosome serum in liposome form for hair, scalp, burn ointments/gel, wound healing). The methods for exosome isolation include but are not limited to the following:

1. Ultracentrifugation.
   a. Conditioned medium is centrifuged at lower speeds to remove cell debris.
   b. Then, the remaining supernatant is centrifuged at high g forces (e.g., 100,000×g) to facilitate the sedimentation of the exosomes.
   c. Exosome pellets are then washed and resuspended in the desired medium.
2. Sucrose Density Centrifugation
   a. Exosomes are separated in a density gradient established by different sucrose concentrations.
   b. The exosome fraction is then isolated and further processed by washing and resuspension in the desired medium.
3. Size Exclusion Chromatography
   a. Conditioned medium is loaded onto a column that allows for the separation of exosomes from other particles based on their size.
4. Precipitation
   a. Conditioned medium is exposed to agents that lower the solubility of exosomes and thereby facilitate their precipitation.
   b. This agent can be polyethylene glycol (PEG) or other suitable polymers or compounds.
   c. Exosomes are then washed and can be resuspended in the medium of choice.
5. Tangential Flow Filtration/Ultrafiltration
   a. Conditioned medium is filtered using tangential flow filters.
   b. Exosomes are retained in the filter (retentate)
   c. The exosomes are washed while conditioned medium is removed.
   d. Exosomes are suspended in the medium of choice.
6. Immunoprecipitation
   a. Exosomes are precipitated from conditioned medium using antibodies targeted to specific exosome proteins.
   b. Exosomes are then released, washed, and resuspended in desired medium.
7. Immunoaffinity/with or without Chromatography
   a. Exosomes are retained on a column or other physical support by antibodies that are targeted to unique exosome proteins.
   b. Exosomes are then washed, released from support, and resuspended in desired medium.
8. Flow-Field Flow Fractionation
   a. Originated as a detection method for exosome populations, it has been recently used to isolate exosomes from conditioned medium.

Liposomes included in the present disclosure are lipid vessel that can contain stabilizing agents, preservatives, and penetration enhancers. Such liposomes have at least one lipid bilayer and can be formed, for example, using lecithin without the use of ethanol or other alcohol because of the latter's adverse effects on exosomes. Other than lecithin (phospholipid aka. Phosphatidylcholine), other examples of lipids that can be used to form liposomes used in embodiments of the present disclosure are phosphatidic acid (phosphatidate) (PA), Phosphatidylethanolamine (cephalin) (PE), Phosphatidylserine (PS), Phosphatidylinositol (PI), Phosphatidylinositol phosphate (PIP), Phosphatidylinositol bisphosphate (PIP2) and Phosphatidylinositol trisphosphate (PIP3), Phosphosphingolipids, Ceramide phosphorylcholine (Sphingomyelin) (SPH), Ceramide phosphorylethanolamine (Sphingomyelin) (Cer-PE), Ceramide phosphoryllipid etc.

Additionally, niosomes can also be used in place or in combination with liposomes even though niosomes may not be as stable as liposomes. Niosomes are vesicles composed of hydrated non-ionic surfactants, such as alkyl-ether, esters, and amides, and cholesterol and can be used as an alternative to liposomes. Niosomes can be made using the same process as is used in making liposomes.

The liposomes used in embodiments of the present disclosure can be present in embodiments of the present disclosure in an amount of about 1.00 wt % to about 20.00 wt %, about 5.0 wt % to about 15 wt %, about 10 wt %.

Embodiments of the present disclosure include mixtures where the exosomes are located outside the liposome, as well as mixtures where the exosomes are located inside the liposome or a mixture of the two.

The compositions with exosome and optionally and preferably with liposomes of the present disclosure, can include additional components added to the mixture, for example, to preservative and maintain the structure and integrity of the exosomes and its contents as well as other benefits. When exosomes disintegrate, they will release their contents and are no longer able to fuse with a living cell. Most released bio compounds will degrade fast, but some proteins may still be able to fulfill their biological function. The additional components can include, for example, dimethyl sulfoxide (DMSO) as well as at least one or more typical preservative compounds including for example, epsilon poly L-lysine, "Linatural," phenoxyethanol, and quaternary ammonium cations, such as, for example, benzalkonium chloride. The pH of the resulting mixtures of the present disclosure can be between about 5 and about 7.5, which is a critical range in which the exosomes should reside. The pH can be adjusted to be within this range using buffers such as ammonium sulfate, sodium citrate, sodium chloride, sodium acetate.

The resulting mixture including exosome, optionally including liposome and/or niosomes and additional components (e.g., a solvent/skin penetrant (e.g., DMSO) and preservative (e.g., epsilon poly L-lysine)) can be maintained for storage prior to use at a temperature of from about −200° C. to about room temperature (about 25° C.). The exosome, a solvent/skin penetrant (e.g., DMSO) and preservative (e.g., epsilon poly L-lysine) composition, optionally including liposomes, embodiments of the present disclosure could maintain the structure and integrity of the exosomes for a time period for as much as two years at a temperature of at most about 4.4° C.

DMSO is a polar aprotic solvent that is preferably included in embodiments of the present disclosure and can deter the presence of clumping of the exosomes as well as act as a solvent/skin penetrant in embodiments of the present disclosure. DMSO can be present in embodiments of the present disclosure in an amount of about 0.001 wt % to about 0.50 wt %, but no more. Other examples of a solvent/skin penetrant that can be used in embodiments of the present disclosure are acetone, DMF (N,N-dimethylformamide), acetonitrile, HMF (hydroxymethylfurfural), crown ethers, fatty acids, essential oils, urea, azone, sodium PCA, etc. These other solvents/skin penetrants can be present in embodiments of the present disclosure in an amount of about 0.001 wt % to about 0.50 wt %, but no more.

Epsilon-poly-L-lysine (ε-PL) is a natural antimicrobial cationic peptide and is the preferable preservative in embodiments of the present disclosure. ε-PL can be present in embodiments of the present disclosure in an amount of about 0.015 wt % to about 0.035 wt %, about 0.025 wt % (0.025% is the maximum currently allowed by the FDA for polylysine). Linatural is a combination of propylene glycol, potassium sorbate, and ethylhexyl glycerin and has been widely used in the cosmetic industry. Linatural can be present in embodiments of the present disclosure in an amount of about 0.5 wt % to about 2.0 wt %. Phenoxyethanol is a preservative used in many cosmetics and personal care products. Phenoxyethanol can be present in embodiments of the present disclosure in an amount of about 0.001 wt % to about 1.00 wt %. (1.0 wt % is the maximum currently allowed by the FDA for phenoxyethanol.)

Other examples of a preservative that can be used in embodiments of the present disclosure are K sorbate, aminobenzoate esters, quaternary ammonium cations and/or compounds, (BZK), benzoic acid/salts, benzyl alcohol, chlorhexidine, chlorocresol, imidurea, bronopol, propionic acid/salts, sorbic acid/salts, phenol, acetate, borates, nitrates etc. The amount of these preservatives should be no more than 0.015 wt %.

Embodiments of the present disclosure may also include one or more humectant/emollients, such for example, butylene glycol, shea butter, squalane, and fatty alcohols like cetyl alcohol hyaluronic acid, glycerin, aloe, elastin, and collagen, glycerin, propylene glycol etc. The one or more humectant/emollients can be present in embodiments of the present disclosure in an amount of about 0.10 wt % to about 10.0 wt %, about 2.0 wt % to about 6.0 wt %, about 4.0 wt %.

Embodiments of the present disclosure may also include one or more excipients, such for example, hemp oil (e.g., full spectrum hemp oil), aloe, vitamins, natural fruit extracts, panthenol, tocopherol acetate, ascorbic acid, niacinamide, menthol, biotin etc. One or more excipients can be present in embodiments of the present disclosure in an amount of about 0.01 wt % to about 10.0 wt %, about 2.5 wt % to about 7.5 wt %, about 5.0 wt %. Other excipients can include thickeners including, for example, natural/synthetic gums i.e., xanthan, algin, CMC, PVP, PVOH, HPMC, methyl cellulose, gum Arabic/acacia, karaya, MVE-MA copolymer, carbomer, etc. The other excipients can be present in embodiments of the present disclosure in an amount of about 0.01 wt % to about 3.0 wt %, about 0.10 wt % to about 1.0 wt %, about 0.2 wt %.

One or more chelating agents can also be optionally added such as for example, citric acid, EDTA, dimercaprol, succimer, penicillamine, trientine and deferrioxamine. The one or more chelating agents can be present in embodiments of the present disclosure in an amount of about 0.05% wt % to about 0.10 wt %, about 0.075 wt %.

Cannabinoids are an active agent and a class of chemical compounds that can be derived from plants (phytocannabinoids) or synthetically produced. Cannabinoids can have local and systemic analgesic, pain relieving, pain treating and anti-inflammatory therapeutic properties. Cannabinoids may also have other medical benefits and/or be useful in treating other medical conditions including, for example, reduction of anxiety and depression, reduction of symptoms like nausea, vomiting and pain related to cancer treatments, reduction of acne, protection of the neural system and benefits for the heart and circulatory system by the lowering of blood pressure. Cannabinoids can also have therapeutic value as a nutrient and can be included in composition and method embodiments of the present disclosure in an effective amount to perform that function.

Examples of phytocannabinoids include Cannabidiol (CBD) including, for example, CBD oil, Cannabinol (CBN) and tetrahydrocannabinol (THC), the latter being a known psychotropic compound and the first two being non-psychotropic. *Cannabis* plants can exhibit wide variation in the quantity and type of cannabinoids they produce. Selective breeding of the plants can be used to control the genetics of plants and modify the cannabinoids produced by the plant. For example, there are strains that are used as fiber (commonly called hemp) and, as a result, have been bred such that they are low in psychoactive chemicals like THC. Such strains (e.g., hemp) used in medicine are, for example, often bred for high CBD content and cannabinoids included herein (unless otherwise stated) have minimal levels of THC (less than 0.3 wt %). Examples of oral or pharmaceutically effective cannabinoids include CBD (for example, full spectrum hemp or CBD oil). Cannabinoid, including, for example, phytocannabinoids including CBD or full spectrum hemp or CBD oil, can be in an amount of about 0.1 wt % to about 20 wt %, about 0.1 wt % to about 10 wt %, about 0.5 wt % to about 6 wt % or about 5.7 wt %. CBD can be in an amount of about 0.1 wt % to about 20 wt %, about 0.1 wt % to about 10 wt %, about 0.5 wt % to about 5 wt %, about 0.5 wt % to about 2 wt % or about 1.9 wt %. Unit dosage formulations of the embodiments of the present disclosure can include cannabinoid, for example, a phytocannabinoid (including for example, CBD or full spectrum hemp or CBD oil) in the amount of about 2 mg. to about 60 mg., about 5 mg. to about 30 mg., about 5 mg to about 15 mg., about 15 mg. to about 30 mg. or about 30 mg. to about 45 mg. Unit dosage formulations of the embodiments of the present disclosure can include CBD in the amount of about 2 mg. to about 30 mg., about 5 mg. to about 30 mg., about 5 mg. to about 15 mg., about 15 mg. to about 30 mg. or about 10 mg. Unit doses of full spectrum CBD or hemp oil content can include an amount of about 2 mg. to about 60 mg. An effective amount of cannabinoid includes an analgesic, pain relieving, pain treating or anti-inflammatory amount of cannabinoid.

Cannabinoids, for example, CBD can have a local and/or a systemic effect and may reduce pain imparting and regulating the endocannabinoid (neurotransmitter of the nervous system) receptor activity. The subsequent body functions that may be regulated include pain, sleep, appetite and immune system response (through, at least, in part, by reducing inflammation).

For the purpose of the present disclosure, the word "cannabinoid" refers to one or more cannabinoids or cannabinoid compounds or oils or extracts from plants (for example, hemp including hemp oil, full spectrum hemp oil, CBD oil, full spectrum CBD oil, *Cannabis sativa* seed oil, etc.) that include one or a plurality of phytocannabinoids.

Hemp oil and full spectrum hemp oil is oil derived from the entire hemp plant except the flower (which contains tetrahydrocannabinol (THC)) and can have over 85 phytocannabinoids which can have a positive synergistic effect as compared to compositions having fewer cannabinoids. There may also be benefits to other components of it (e.g., terpenes). Such benefits and effect may include faster penetration and/or permeation of the therapeutic components thereof. Full spectrum hemp oil can include full spectrum hemp oil that has been purified to include less than the below stated amounts of one or more of the following impurities: Aflatoxins BI, 82, G1, G2 (fats, oils, lecithin, egg powder): <0.1 μg/kg of each of Aflatoxin B1, Aflatoxin B2, Aflatoxin GI and Aflatoxin G2, Sum of all positive Aflatoxins <0.4 μg/kg.
GlyphosatelAMPAiGlufosinate: <0.1 mg/kg of each of Glufosinate, Glyphosate and Aminomethylphosphonic acid (AMPA)
Mercury: <0.02 mg/kg
Arsenic: <0.03 mg/kg
Cadmium: <0.01 mg/kg
Lead: <0.05 mg/kg.

Hemp oil and full spectrum hemp oil can include less than about 0.3 wt % THC.

Embodiments of the present disclosure also include methods of use of the exosome composition embodiments of the present disclosure that are applied to bone and tissue and used to promote wound healing as well as bone and tissue growth, for example, used in surgical tissue and bone graft procedures. Embodiments of the present disclosure can also be topically applied to the skin of a person, for example, to the scalp or other skin surface, to promote hair growth as well as to treat skin defects such as aging, atopic dermatitis, and wounds.

Embodiments of the present disclosure can also include additional therapeutic compositions for topical or internal administration that may also include other therapeutic or pharmaceutical actives such as, for example, menthol, camphor and cannabinoids (e.g., hemp oil, cannabidiol) as well as the methods of making and using/treating using such therapeutic compositions. The majority of beneficial components are in the exosomes. However, stem cells also secrete cytokines and growth factors (natural components) into the surrounding medium which are not enclosed in exosomes. If liposomes are created with exosomes and growth factors/cytokines present, then these can also be enclosed into the liposomes.

Methods of use of embodiments of the present disclosure can be include gastrointestinal delivery (oral delivery, sublingual delivery, buccal delivery, rectal delivery), parenteral delivery (intradermal delivery, sub-cutaneous delivery, intramuscular delivery, intravenous delivery) and Topical (transdermal patches, instillations, irrigation or douching, epidermic or enepidermic routes, throat paints, inhalation routes).

The embodiments of the present disclosure including exosomes can be made at about room temperature by combining the above described exosome suspensions in approximately isotonic aqueous solutions of, for example, 0.9 wt % sodium or phosphate buffered saline with a solvent/skin penetrant (e.g., DMSO) and preservative (e.g., epsilon poly L-lysine) and optionally additional ingredients disclosed herein (e.g., humectant/emollients, thickeners, chelating agents, etc.). Additional water at about room temperature can be added (isotonic or distilled) to adjust the exosome concentration. Buffers can be added at about room temperature to adjust the pH, if necessary, to between about 5.0 to about 7.5. The salinity can then optionally be adjusted at about room temperature to make the resulting mixture approximately isotonic. The resulting mixture can then be maintained at between about −200° C. and room temperature, preferably, frozen if to be stored.

The embodiments of the present disclosure including exosomes and liposomes and/or nicosomes where it is desired to have liposomes and/or nicosomes with exosomes included therein can be made at about room temperature by combining the above described exosome suspensions in approximately isotonic aqueous solutions of, for example, 0.9 wt % sodium or phosphate buffered saline with at least one lipid to form the liposomes and/or nicosomes (e.g., lecithin). Then a solvent/skin penetrant (e.g., DMSO) and preservative (e.g., epsilon poly L-lysine) and optionally additional ingredients disclosed herein (e.g., humectant/ emollients, thickeners, chelating agents, etc.) are added at about room temperature. Additional water can be added at about room temperature (isotonic or distilled) to adjust the exosome concentration. Buffers can be added at about room temperature to adjust the pH, if necessary, to between about 5.0 to about 7.5. The salinity can then optionally be adjusted at about room temperature to make the resulting mixture approximately isotonic. The resulting mixture can then be maintained at between about −200° C. and room temperature, preferably, frozen if to be stored.

The embodiments of the present disclosure including exosomes and liposomes and/or nicosomes where it is desired to have the exosomes external to the liposomes and/or nicosomes can be made at about room temperature by adding at least one a lipid to water to form the liposomes and/or nicosomes (e.g., lecithin). Then a solvent/skin penetrant (e.g., DMSO) and preservative (e.g., epsilon poly L-lysine) and optionally additional ingredients disclosed herein (e.g., humectant/emollients, thickeners, chelating agents, etc.) are added at about room temperature. The above described exosome suspensions in approximately isotonic aqueous solutions of, for example, 0.9 wt % sodium or phosphate buffered saline can be added at about room temperature. Additional water can be added (isotonic or distilled) at about room temperature to adjust the exosome concentration. Buffers can be added at about room temperature to adjust the pH, if necessary, to between about 5.0 to about 7.5. The salinity can then optionally be adjusted at about room temperature to make the resulting mixture approximately isotonic. The resulting mixture can then be maintained at between about −200° C. and room temperature, preferably, frozen if to be stored.

The embodiments of the present disclosure including exosomes and liposomes and/or nicosomes where it is desired to have some exosomes external to the liposomes and/or nicosomes and liposomes and/or nicosomes with some exosomes included therein can be made at about room temperature by combining a portion of the above described exosome suspensions in approximately isotonic aqueous solutions of, for example, 0.9 wt % sodium or phosphate buffered saline with at least one lipid to form the liposomes and/or nicosomes (e.g., lecithin). Then a solvent/skin penetrant (e.g., DMSO) and preservative (e.g., epsilon poly L-lysine) and optionally additional ingredients disclosed herein (e.g., humectant/emollients, thickeners, chelating agents, etc.) are added at about room temperature. Another portion of the above described exosome suspensions in approximately isotonic aqueous solutions of, for example, 0.9 wt % sodium or phosphate buffered saline can then be added at about room temperature. Additional water can be added (isotonic or distilled) at about room temperature to adjust the exosome concentration. Buffers can be added at about room temperature to adjust the pH, if necessary, to between about 5.0 to about 7.5. The salinity can then optionally be adjusted at about room temperature to make the resulting mixture approximately isotonic. The resulting mixture can then be maintained at between about −200° C. and room temperature, preferably, frozen if to be stored.

Example 1—Exosome-containing Composition Formula

| Item # | Ingredient | Function | wt % in Example | Approximate lower wt % amount acceptable | Approximate upper wt % amount acceptable |
|---|---|---|---|---|---|
| 1 | Water | Solvent | 78.35 | 60.00 | 90.00 |
| 2 | Butylene glycol | Humectant | 4.00 | 0.10 | 10.00 |
| 3 | Lecithin | Phospholipid | 11.00 | 1.00 | 20.00 |
| 4 | ε-poly-l-lysine | Preservative | 0.05 | 0.00 | 0.50 |
| 5 | K Sorbate | Preservative | 0.10 | 0.03 | 0.20 |
| 6 | DMSO | Solvent | 0.50 | 0.01 | 2.00 |
| 7 | Exosome | Active | 1.00 | 0.01 | 5.00 |
| 8 | Hemp Oil | Excipient(s) | 5.00 | 1.00 | 10.00 |
| | | Total | 100.00 | | |

Example 2—Method of Making the Exosome-Containing Composition in Example 1 Formula 1. Lecithin was vigorously mixed with 40 wt % water until homogenous about room temperature (about 25° C.).
2. QS remaining water as per the formula in Example 1 to mixture and added ε-poly-l-lysine, DMSO, K Sorbate, butylene glycol, and hemp oil at about room temperature (about 25° C.). Other excipients can be added as needed, take away from the water (i.e., q.s.—quantum satis) Such excipients are thickeners (synth and natural gums), emollients, fragrance, etc. Additionally, buffers such as ammonium sulfate, sodium citrate, sodium chloride, sodium acetate could be added to maintain a pH of about 5.0 to about 7.5.
3. Chelating agents can also be optionally added . . . i.e. citric acid, EDTA, dimercaprol, succimer, penicillamine, trientine, deferrioxamine, etc.) about room temperature (about 25° C.).
4. Exosomes were then added last to the mixture to form a mixture about room temperature (about 25° C.) where the exosome is outside the liposome.

Example 3—Method of Making the Exosome-Containing Composition

1. Lecithin was vigorously mixed with 40 wt % water and the exosomes until homogenous about room temperature (about 25° C.).
2. QS remaining water to mixture and added ε-poly-l-lysine, DMSO, K Sorbate, butylene glycol, and hemp oil about room temperature (about 25° C.). Other excipients can be added as needed, take away from the water about room temperature (about 25° C.). Such excipients are thickeners (synth and natural gums), emollients, fragrance, etc. Additionally, buffers such as ammonium sulfate, sodium citrate, sodium chloride, sodium acetate could be added to maintain a pH of about 5.0 to about 7.5.
3. Chelating agents can also be optionally added at about room temperature i.e., citric acid, EDTA, dimercaprol, succimer, penicillamine, trientine, deferrioxamine, etc.) about room temperature (about 25° C.).

Since the exosomes are added to the Lecithin mixture at the beginning of the process, the exosome is inside the liposome. However, if exosomes are added at the end of the process, the exosome will be outside the liposome.

All publications, including but not limited to, issued patents, patent applications, and journal articles, cited in this application are each herein incorporated by reference in their entirety.

Thus, while there have been shown, described and pointed out, fundamental novel features of the present disclosure as applied to the exemplary embodiments thereof, it will be understood that various omissions and substitutions and changes in the form and details of devices and methods illustrated, and in their operation, may be made by those skilled in the art without departing from the spirit or scope of the present disclosure. Moreover, it is expressly intended that all combinations of those elements and/or method steps, which perform substantially the same function in substantially the same way to achieve the same results, are within the scope of the present disclosure. Moreover, it should be recognized that structures and/or elements and/or method steps shown and/or described in connection with any disclosed form or embodiment of the present disclosure may be incorporated in any other disclosed or described or suggested form or embodiment as a general matter of design choice. It is the intention, therefore, to be limited only as indicated by the scope of the claims appended hereto.

This written description uses examples as part of the disclosure, including the best mode, and also to enable any person skilled in the art to practice the disclosed implementations, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

While there have been shown, described and pointed out, fundamental features of the present disclosure as applied to the exemplary embodiments thereof, it will be understood that various omissions and substitutions and changes in the form and details of compositions, devices and methods illustrated, and in their operation, may be made by those skilled in the art without departing from the spirit or scope of the present disclosure. Moreover, it is expressly intended that all combinations of those elements and/or method steps, which perform substantially the same function in substantially the same way to achieve the same results, are within the scope of the present disclosure. Moreover, it should be recognized that structures and/or elements and/or method steps shown and/or described in connection with any disclosed form or embodiment of the present disclosure may be incorporated in any other disclosed or described or suggested form or embodiment as a general matter of design choice. It is the intention, therefore, to be limited only as indicated by the scope of the claims appended hereto.

The invention claimed is:

1. A composition, comprising:
a plurality of liposomes, including
a plurality of exosomes where the plurality of exosomes are positioned inside the plurality of liposomes; and
stabilizing agents inside the plurality of liposomes including dimethyl sulfoxide and epsilon poly L-lysine where the epsilon poly L-lysine maintainsa the structure and integrity of the plurality of exosomes and prevent clumping of the exosomes.

2. The composition of claim 1, wherein the plurality of exosomes includes placental cell exosomes, stem cell exosomes or a mixture thereof.

3. The composition of claim 1, wherein the plurality of exosomes is present in an amount of about 0.25 wt % to about 1.00 wt %, about 0.50 wt %, about 10 million to about 20 trillion exosomes per 1 ml volume or about 1 billion exosomes per 1 ml volume.

4. The composition of claim 1, wherein the dimethyl sulfoxide is in an amount of about 0.001 wt % to about 0.50 wt %.

5. The composition of claim 1, wherein the epsilon poly L-lysine is in an amount of about 0.015 wt % to about 0.035 wt % or about 0.025 wt %.

6. The composition of claim 1, wherein the pH of the composition ranges from between about 5 to about 7.5.

* * * * *